(12) United States Patent
Milanovic

(10) Patent No.: US 7,686,931 B2
(45) Date of Patent: Mar. 30, 2010

(54) SAFETY DEVICE FOR AN INSERTION ELECTRODE DEVICE

(75) Inventor: Jelena Milanovic, Flslisbach (CH)

(73) Assignee: Mettler-Toledo AG, Greifensee (CH)

( * ) Notice: Subject to any disclaimer, the term of this patent is extended or adjusted under 35 U.S.C. 154(b) by 1166 days.

(21) Appl. No.: 10/814,280

(22) Filed: Apr. 1, 2004

(65) Prior Publication Data

US 2004/0194563 A1    Oct. 7, 2004

(30) Foreign Application Priority Data

Apr. 3, 2003    (DE) ................. 103 15 338

(51) Int. Cl.
*G01N 27/30*    (2006.01)

(52) U.S. Cl. ...................... 204/415; 204/433

(58) Field of Classification Search ................ 204/415, 204/416, 417, 418, 419, 420, 433
See application file for complete search history.

(56) References Cited

U.S. PATENT DOCUMENTS

| | | | |
|---|---|---|---|
| 4,008,141 A | 2/1977 | Kotani et al. | |
| 4,176,032 A * | 11/1979 | Stevenson, Jr. | ............... 204/415 |
| 4,383,908 A | 5/1983 | Phelps et al. | |
| 6,000,290 A | 12/1999 | Benton et al. | |
| 6,328,515 B1 * | 12/2001 | Donovan | ..................... 411/386 |

FOREIGN PATENT DOCUMENTS

| | | |
|---|---|---|
| CH | 673 895 A5 | 4/1990 |
| DE | 1 887 956 | 2/1964 |
| DE | 7246794 | 5/1975 |
| DE | 25 44 360 | 12/1978 |
| EP | 0 590 290 A1 | 8/1993 |
| GB | 2271853 | 4/1994 |

OTHER PUBLICATIONS

European Search Report in corresponding EP Application No. 04101345 dated Dec. 3, 2004 (2 pages).

* cited by examiner

*Primary Examiner*—Kaj K Olsen
(74) *Attorney, Agent, or Firm*—Buchanan Ingersoll & Rooney PC

(57) ABSTRACT

A insertion electrode device, which is configured for installing a sensor probe in a container for a measuring medium, includes a probe housing that can be attached to the container and has a probe protector tube serving to receive, hold and guide the sensor probe. The sensor probe has a coupling for electrical connections, and the probe housing is equipped with a protective sleeve to protect the coupling from mechanical stress and moisture. The protective sleeve is connectable to the probe protector tube. A safety adapter is coupled to the end of the probe protector tube that is outside the container. The safety adapter engages a recess of the sensor probe or reaches over a step of the sensor probe and thereby secures the latter against moving in the axial direction.

17 Claims, 3 Drawing Sheets

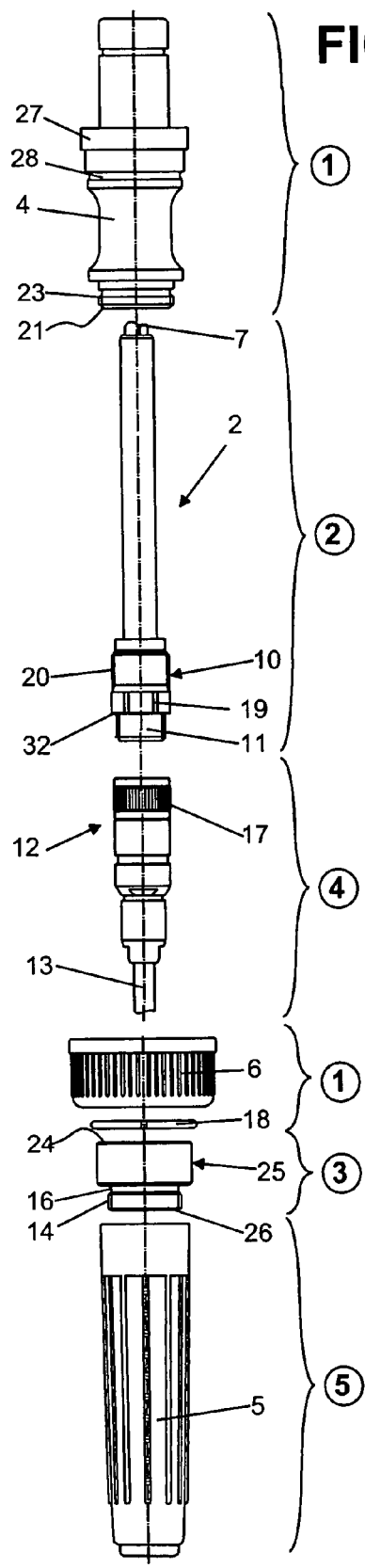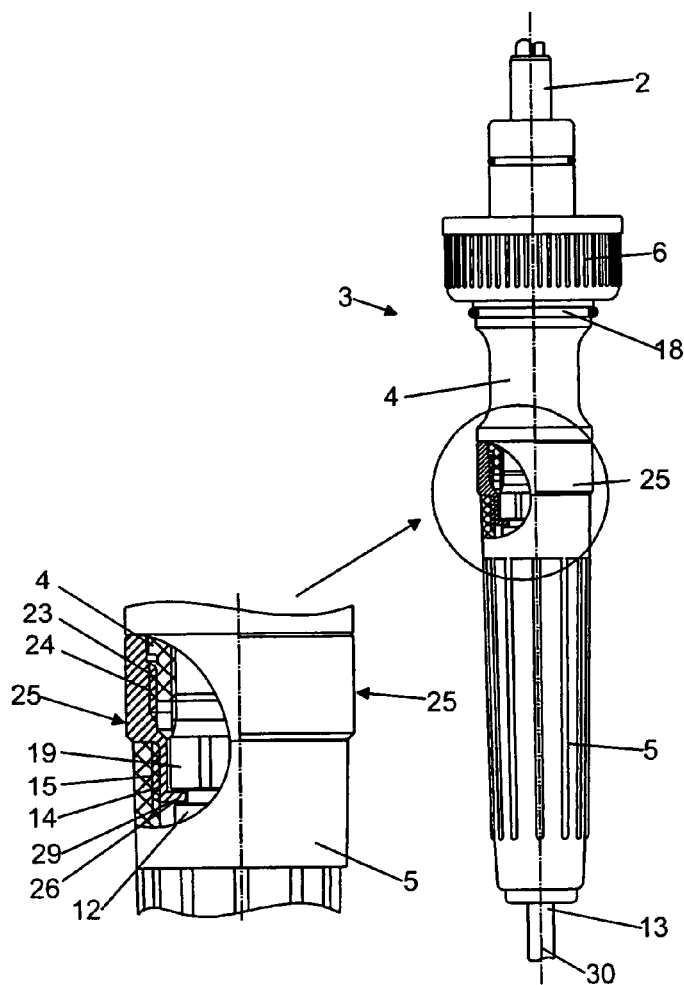
FIG. 4
FIG. 3

SAFETY DEVICE FOR AN INSERTION ELECTRODE DEVICE

CROSS REFERENCE TO RELATED APPLICATIONS

This application claims priority under 35 U.S.C. §119 to German Application No. 10315338.1 filed in Germany on 3 Apr. 2003, the entire contents of which are hereby incorporated by reference in their entirety.

BACKGROUND

The invention relates to an insertion electrode device for installing a sensor electrode (also referred to as sensor probe) in a container for a measuring medium. The assembly includes a probe housing (also referred to as probe holder) that can be attached to the container and contains a probe protector tube which serves to receive, hold and guide a sensor probe. The probe has a coupling for electrical connections, and the probe housing has a protective sleeve that can be connected to the probe protector tube to protect the electrical coupling from mechanical stress and moisture.

The types of sensor probes used in insertion electrode devices of this kind include oxygen probes, pH-measuring probes, conductivity probes, etc. The probes consist mostly of glass. In process control applications, the probes are installed with preference in reactors, mixing containers, or flow-through pipes, where the probes serve to determine characteristic parameters of a measuring medium contained in one of the aforementioned vessels or conduits. To perform this function, a probe is installed in a housing or holder. The probe holder serves to hold, guide and protect the probe. In particular, the probe holder establishes a connection between the probe and the container in which the probe is installed, i.e. for example a reactor, a mixing container or a flow-through pipe. A distinction is made between so-called static probe holders and retractable probe holders or housings. With the latter, the installed probe can be retracted into a rinsing chamber and cleaned during the process that the probe serves to monitor.

A so-called static probe holder does not offer the possibility of cleaning the probe during a process. It serves only to hold, guide and protect the probe. A probe housing or probe holder of this type is described in CH 673 895 A5. The housing in CH 673 895 A5 is part of a glass electrode device or insertion electrode device, for example for pH measurements or redox measurements. The housing consists of a housing top and a housing bottom, where the latter is configured as an immersion tube. The housing top can be attached to a socket of a reactor vessel, for example by means of a sleeve nut. A sensor probe, for example a glass electrode, is arranged inside the housing with the electrode shaft extending through the immersion tube and protruding into the medium inside the reactor vessel. The glass electrode is secured in the housing by means of a nut and a back-up ring.

A retractable holder or housing which is operated by compressed air is disclosed in EP 0 590 290 A1. It is equipped with a safety device which prevents the actuation of the retractable housing by letting the pressurized air escape through an opening when no sensor probe is installed, but keeps the opening closed when a probe is seated in the housing.

FIG. 1 represents, partly in a sectional view (in the left-hand part of the drawing), an example of a insertion electrode device 1 according to the state of the art. The device includes a static probe holder 3 that is suitable for installing a probe 2, in particular a glass electrode. The static probe holder 3 surrounding the probe 2 consists of a probe protector tube 4 and a protective sleeve 5. Near the end that faces towards the container in which the probe 2 is to be installed, the probe holder 3 has a process adapter 6 which is configured as a sleeve nut in the illustrated example. The process adapter 6 serves to screw the probe holder 3 to a connector socket (not shown in the drawing) of a container. Thus, a part of the probe protector tube reaches into the container (likewise not shown in the drawing). A probe 2, which is seated in the probe protector tube 4 extends likewise into the container and protrudes from the probe protector tube 4, so that a membrane 7 at the tip of the probe is immersed in the measuring fluid. A seal ring 8 prevents measuring fluid from entering between the probe 2 and the probe protector tube 4. A further seal ring 9 serves to seal the probe protector tube against the socket of the container. A third ring 18 retains the process adapter 6, so that the process adapter can move but remains captive in its position on the probe protector tube 4.

At the end of the probe 2 which during a process is located outside of the container, i.e., below the process adapter 6 in the representation of the drawing, the probe 2 has a probe header 10 with a connector terminal 11 (not shown in detail in FIG. 1) that connects to a plug 12 of an electrical cable 13. The probe header 10 has a hexagonal portion 19, so that it can be gripped and held by hand when connecting the cable plug. The plug 12 has a knurled sleeve 17 with an internal thread (not visible in FIG. 1) which screws onto an external thread (likewise invisible in the drawing) of the connector terminal 11 to secure the connection.

The probe 2 itself is screwed into the probe protector tube by means of an external thread 20 that mates with an internal thread 21 at the end of the probe protector tube that faces away from the process container. The same end of the probe protector tube 4 carries an external thread 24 which serves to attach a protective sleeve 5. For the purpose of this connection, the protective sleeve 5 is equipped with an internal thread 23 which is preferably formed in a connector part 22 which is solidly attached to the protective sleeve 5, for example by and adhesive bond. Of course, the protective sleeve could also be made of one piece. As an additional measure, a sealing compound is applied to the screw connection between the protective sleeve 5 and the probe protector tube 4, which serves in particular to prevent moisture from penetrating into the area of the electrical connection of the probe 2. When separated from the probe protector tube 4, the protective sleeve 5 can be moved along the cable 13 as well as turned about the cable 13 for making the screw connection, as the passage of the cable through the protective sleeve 5 is formed by a grommet 31 which can consist of rubber, so that it forms a good seal but is flexible at the same time.

From the foregoing description, one can establish for example the following procedure for the installation of a probe holder 3 on a container and the installation of a probe 2 in the probe holder according to the state of the art.

A. Insert the probe protector tube 4 into the connector socket and attach the process adapter 6 to the connector socket.

B. Insert the probe 2 into the probe protector tube 4 and screw the probe 2 tightly into the internal thread 21.

C. Connect the plug 12 to the socket 11 of the probe header 10 and screw the knurled sleeve 17 tightly in place D. Screw the protective sleeve 5 onto the probe protector tube 4, applying a sealing compound to the screw threads.

However, the design of the insertion electrode device is also compatible with an installation procedure in which the aforementioned steps are performed in a different sequence. One could for example switch the steps B and C.

The disassembly is performed in reverse sequence, and it is again possible to switch the sequence of steps. It could occur, for example, that after unscrewing the protective sleeve 5 from the sleeve protector tube 4, a user may intend to loosen the screw connection of the knurled sleeve 17 which holds the plug 12 connected to the terminal 11, but if the user neglects to hold the probe 2 by its hexagonal portion 19, he could inadvertently loosen the screw connection between the probe header 10 and the probe protector tube 4, and thereby remove the entire probe 2 together with the plug connection from the probe housing 3. Removing the probe while a process is running, could have disastrous consequences. For example, the chemicals in the reactor could escape to the outside, which is particularly dangerous if the process in the reactor runs at above-ambient pressure. One cannot ignore the risk of personal injury that exists under these conditions.

SUMMARY

Exemplary embodiments are disclosed which can provide an increased degree of safety for an insertion electrode device with a probe holder installed in a container and a sensor probe installed in the probe holder. The proposed safety measures can be made compatible with existing probe holders and sensor probes so that they can be retrofitted to a customer's existing equipment.

An exemplary insertion electrode device designed for the installation of a probe in a container for a measuring medium includes a probe housing that is attached to the container and has a probe protector tube serving to receive, hold and guide the sensor probe. The sensor probe has a coupling for electrical connections, and the housing is equipped with a protective sleeve to protect the electrical coupling from mechanical stress and moisture. The protective sleeve is configured so that it can be attached to the probe protector tube. A safety adapter can be connected to the end of the probe protector tube that is located outside of the container. The safety adapter engages a recess of the sensor probe or reaches over a step of the sensor probe and can thereby secure the latter from moving in the axial direction.

Substantially no design changes are made in exemplary sensor probes as well as the probe holders to ensure a problem-free and therefore cost-effective interchangeability with the addition of the safety adapter to the device, so that the insertion electrode device no longer presents the risk that a probe can inadvertently be separated from the probe holder during a process. A user can be forced to follow a prescribed procedural sequence when removing the insertion electrode device from the container. With an exemplary safety adapter, the coupling for the electrical connections can be safely disconnected from the probe. This can be a required operating routine in case of an electrical malfunction.

In an exemplary embodiment of the insertion electrode device, the probe has a probe header with a step that the safety adapter can bear against.

In a further exemplary embodiment, the probe header is equipped with an external screw thread that allows the probe to be screwed into an internal screw thread of the probe protector tube.

In a further advantageous embodiment of the insertion electrode device, the coupling for the electrical leads has the form of a plug-in connection which is secured by a sleeve that holds one part of the plug connection and is screwed onto the other part of the connection.

The protective sleeve can be releasably connectable to the safety adapter, in particular by means of a screw connection.

In a particularly advantageous embodiment, the part of the safety adapter that bears against the probe header includes a ring-shaped collar. However, the part that bears against the probe header can also include at least two projections designed to bear against the probe header or, as an alternative, at least two pin-shaped spring elements or, as a further alternative, an annular spring element.

BRIEF DESCRIPTION OF THE DRAWINGS

The invention will be further explained hereinafter with reference to drawings, wherein:

FIG. 3 represents an exemplary side view of the insertion electrode device of FIG. 2, wherein the portion in which the safety adapter is located is cut open and also shown in an enlarged detail view;

FIG. 4 represents an exemplary side view of the insertion electrode device with a probe housing and a probe to illustrate how the device is put together and taken apart;

DETAILED DESCRIPTION

Figure 1:
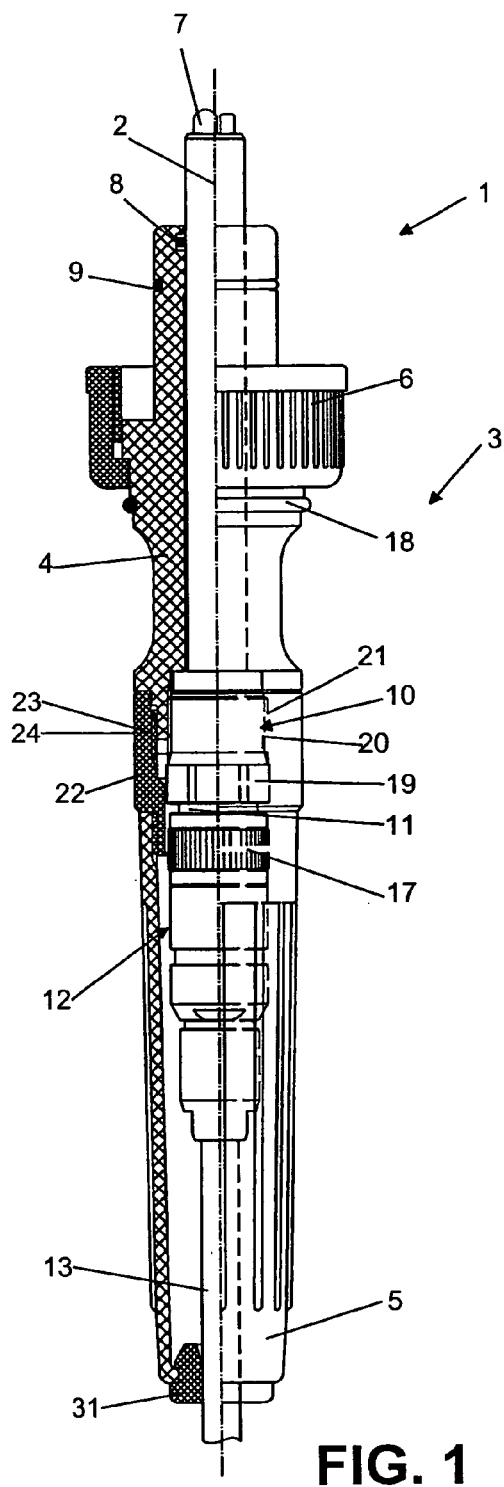
FIG. 1 represents an exemplary insertion electrode device according to the state of the art.
Figure 2:
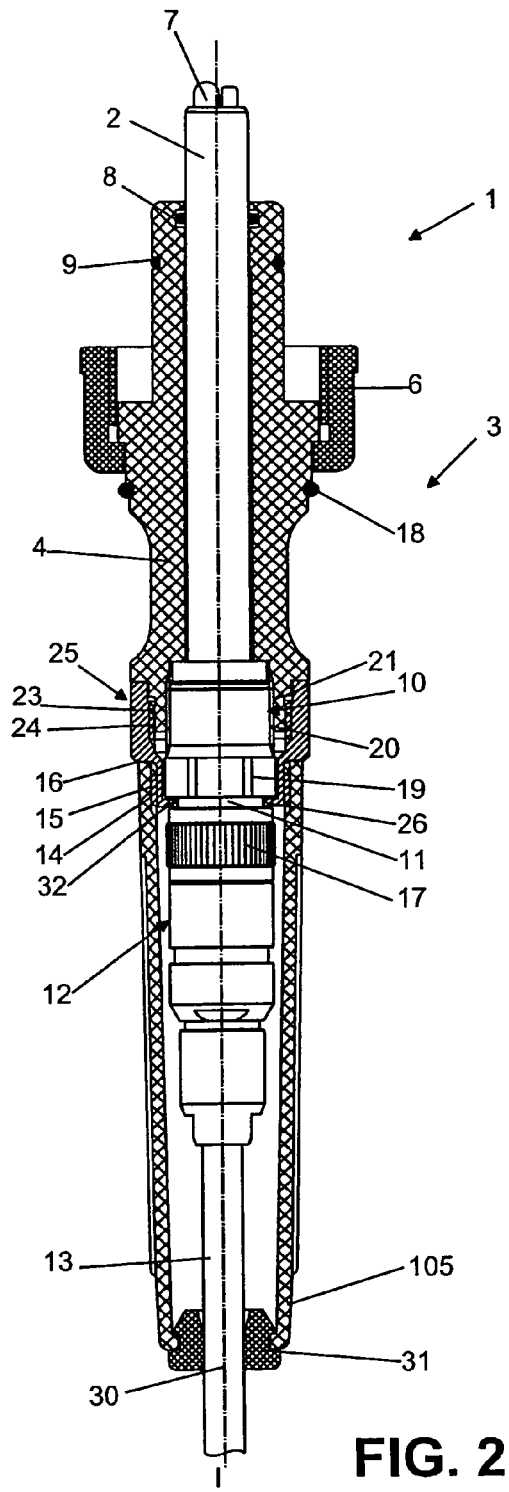
FIG. 2 represents an exemplary insertion electrode device with a safety adapter shown in a sectional view.

FIG. 2 shows a sectional view of an exemplary insertion sensor electrode device with a probe holder 3 in which a probe 2 is installed. Elements that are identical to those described in the context of the device shown in FIG. 1 have been given the same reference symbols and will not be described again. The device of FIG. 2 includes a safety adapter 25 which is positioned between the probe protector tube 4 and a protective sleeve 105. If necessary, the latter may be of a modified design. To avoid an unnecessary increase in the overall lengthwise dimensions of the probe housing 3, it is possible to omit the connector part 22 of the original protective sleeve 5, in which case the original protective sleeve 5 can be replaced by a protective sleeve 105 which can be screwed directly onto the safety adapter 25 without a connector part 22. The protective sleeve 105 can be provided with an internal screw thread 15 that is matched to an external screw thread 14 of the safety adapter 25. However, in an exemplary embodiment, the screw thread 23 is identical to the screw thread 14, and the screw thread 15 is identical to the screw thread 24, so that the protective sleeve can also be screwed onto the safety adapter with the connector part 22 left in place. Furthermore, as mentioned previously, this portion of the protective sleeve can also be made of one piece, i.e., without the adhesive-bonded connector part. To join the protective sleeve 5, 105 to the safety adapter 25 in a form-fitting manner, the safety adapter 25 has a shoulder 16, so that when the protective sleeve 5, 105 is screwed on, it is seated tightly against the shoulder 16.

The safety adapter 25 is distinguished by a collar 26 that is inward-oriented towards the symmetry axis 30 of the insertion sensor electrode device 1. In the installed position of the safety adapter, the collar 26 surrounds the hexagonal portion 19 of the probe header 10 and in particular reaches over and preferably bears against the step 32 that lies between the hexagonal portion 19 and the part of the connector terminal 11 that protrudes from the portion 19 (see in particular FIG. 4). The probe 2 is thereby retained in its installed position in the probe protector tube. This configuration of the safety adapter 25 can dictate a fixed procedure for the installation as well as the removal of the probe holder 3 and the probe 2, such that it is not possible to switch the sequence of steps. This ensures that when the screwed-on sleeve 17 is opened, which retains the plug 12 in the terminal 11, one cannot inadvertently release the probe 2 from the probe holder 3.

FIG. 3 gives an exemplary side view of the insertion electrode device of FIG. 2. The part of the device where the safety adapter 25 is arranged is shown cut away and additionally represented in an enlarged detail view. The collar 26 of the safety adapter 25 reaches into a recess 29 of the probe 2, for example a gap between the step 32 and the sleeve 17 of the plug 12.

FIG. 4 shows an exemplary insertion electrode device 1 in a side view in a disassembled state. Based on this illustration, the details of an exemplary assembly procedure can be described as follows:

1. Insert the probe protector tube 4 of the probe holder 3 into the connector socket that is, e.g., part of a reactor. Position the process adapter 6 against the ring ledge 27 of the probe protector tube 4 and secure the process adapter by installing the ring 18 in the groove 28. Fasten the process adapter 6 to the connector socket.
2. Insert the probe 2 into the probe protector tube 4 up to the probe header 10. Screw the external screw thread 20 of the probe header 10 tightly into the internal thread 21 of the probe protector tube 4 until the probe is securely seated in the probe protector tube. Both screw threads can be standardized threads, for example according to the metric thread specification PG 13.5.
3. Place the safety adapter 25 over the end of the probe protector tube 4 and over the part of the probe header 10 that protrudes from the probe protector tube, specifically over the connector terminal 11. Screw the safety adapter 25 onto the probe protector tube 4 until the collar 26 reaches over the hexagonal portion 19 of the probe header 10, preferably so that the collar 26 is seated against the step 32 between the hexagonal portion 19 and the connector terminal 11. This provides an additional fixation for the probe 2 in the probe protector tube 4 of the probe holder 3. At least, however, the mobility of the sensor probe in its lengthwise direction is strongly constrained. By applying a sealing compound to the threads before screwing the parts together, the connection can be additionally protected so that moisture and dust cannot penetrate between the probe 2 and the safety adapter 25 or between the probe 2 and the probe protector tube 4.
4. Only after all of the preceding operations have been completed, can the plug 12 be connected to the connector terminal 11 of the probe header 10 and secured by means of the knurled sleeve 17. The collar 26 now reaches into the gap 29 (see FIG. 3, enlarged detail) that is left between the hexagonal portion 19 and the plug 12.
5. Screw the protective sleeve 5 onto the safety adapter 25, which is now connected to the probe protector tube 4. The aforementioned sealing compound can also be applied to the connection between the protective sleeve 5 and the safety adapter 25.

The disassembly of the installed sensor probe and probe holder is performed in reverse order:

5'. Unscrew the protective sleeve 5.
4'. Loosen the sleeve 17 and remove the plug 12 from the connector terminal 11.
3'. Remove the safety adapter 25 from the probe protector tube 4.
2'. Remove the probe 2 from the probe protector tube 4.
1'. Unscrew the process adapter 6 from the container.

In an exemplary embodiment, strict following of this sequential order can be required; for example, due to the collar 26 reaching over the step 32 of the hexagonal portion 19, one has to first unscrew the sleeve 17 that secures the connection between the plug 12 and the connector terminal 11, before the safety adapter 25 itself can be taken off. Only after the safety adapter has been taken off the probe 2 can be removed from the probe protector tube 4. Thus, the arrangement forces the user to strictly adhere to the prescribed order of disassembly steps and to be aware of each step, so that it is not possible to inadvertently release the probe 2 from the probe holder 3.

Figure 5:
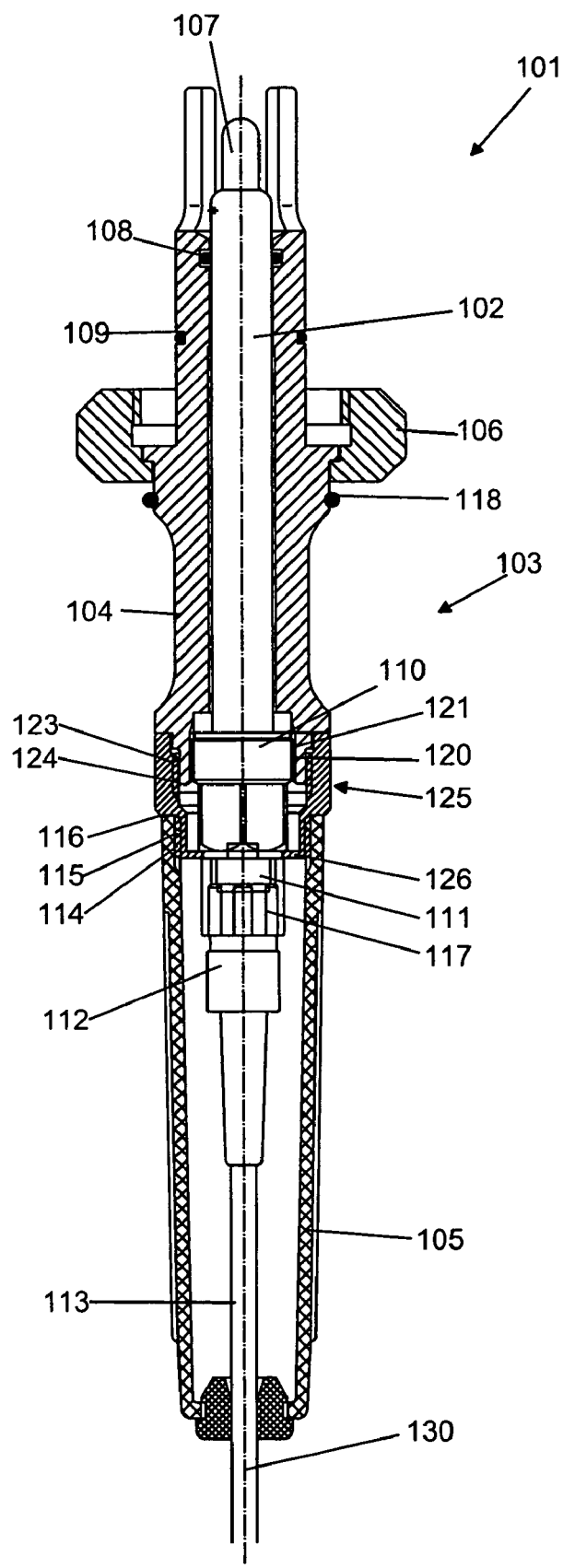
FIG. 5 represents a different embodiment of an exemplary insertion electrode device with a modified safety adapter.

FIG. 5 presents a sectional view of a second exemplary embodiment of a insertion electrode device 101 with a modified probe holder 103, in which a likewise modified probe 102 is installed. The probe protector tube 104 is extended at the end that is inserted in a container, whereby the membrane 107 is better protected during the process. The seal rings 108 and 109 prevent the measuring medium from entering, respectively, the probe protector tube 104 and the socket. The process adapter 106 in this embodiment includes a clamp ring. Of course, one could also use a flange that would be fastened with screws to a matching flange on a socket of the container. The clamp ring, too, is secured by means of a ring 118. The probe header 110 of the probe 102 is screwed into the probe protector tube 104 by means of the standardized threads 120 and 121. The safety adapter 125, which is dimensionally modified in comparison to the safety adapter 25 (FIGS. 2 to 4), is screwed onto the probe protector tube 104 by means of the threads 123 and 124. The plug-in connection between the connector terminal 111 and the plug 112 of the cable 113 is secured by means of a sleeve 117. A protective sleeve 105, which is screwed onto the safety adapter by way of the threads 114 and 115, rests against a shoulder 116. The device can be configured such that the assembly and disassembly steps again have to be performed in strict sequential order in accordance with the steps 1 to 5 and 5' to 1', respectively.

The collar 26, 126, which in the representation of FIGS. 2 to 5 extends as a ring around the safety adapter can also have the shape of two projections, can be diametrically opposed, or a plurality of projections at equal angular intervals, which extend in the direction towards the symmetry axis 30, 130 of the device. When the safety adapter 25, 125 is screwed on according to assembly step 3 of the foregoing description, the projections reach over the probe header 10, 110 and thereby retain the latter in the probe protector tube 4, 104 of the probe holder 3, 103.

It is further possible to use spring elements as retainer devices in the safety adapter. For example, instead of the projections or the collar 26, 126 described above, two or more spring pins could be arranged on the safety adapter in such a manner that a deviation from the lock-step procedure would be possible in the assembly phase, but would be absolutely prevented in the disassembly phase. This can be achieved for example with spring pins aligned perpendicular to the inside surface of the safety adapter, if the end surface of each pin is sloped so that in the installed position of the safety adapter the greatest length of each pin is on the side that faces the probe header 10, 110.

With the elastic spring elements according to the foregoing concept, a probe that is already attached to the plug 12, 112 for the electrical connection could be screwed into the probe protector tube after the latter has already been fitted with the safety adapter. Conversely, however, the plug connection has to be released first, before the safety adapter can be unscrewed.

A ring-shaped spring element that surrounds the safety adapter in place of the collar would perform a similar function.

An insertion electrode device has been described in reference to the example of a static probe holder. It is self-evident, that the insertion electrode device can also contain a retractable probe holder as disclosed, e.g., in EP 0 590 290 A1, where the retractable probe holder would be equipped with a safety adapter as described herein. Further exemplary embodiments are not restricted to insertion electrode devices in which the connections between the probe and the probe protector tube and/or between the probe protector tube and the protective sleeve and/or the securing of the retainer sleeve for the plug connection are configured as screw connections. For example, one or more of these connections could be realized in the form of bayonet connections.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. An insertion electrode device for installing a sensor probe in a container for a measuring medium, with the device comprising:
    a probe housing configured for attachment to a container;
    a probe protector tube to receive, hold, and guide a sensor probe;
    a safety adapter that is coupled to an end of the probe protector tube and over a portion of the probe header that protrudes from the end of the probe protector tube, the safety adapter having means for preventing bi-axial movement of the sensor probe, said means being configured to interact with the sensor probe by one of engaging a recess of the sensor probe or reach over a step of the sensor probe; and
    a coupling for electrical connections of the sensor probe, wherein the probe housing has a protective sleeve configured for connection to the probe protector tube to protect the electrical coupling from mechanical stress and moisture,
    wherein the safety adapter is screwed onto the probe protector tube so that the means for preventing bi-axial movement of the sensor probe are over the portion of the probe header.

2. The insertion electrode device according to claim 1, wherein the safety adapter secures the sensor probe from being inadvertently released from the probe protector tube.

3. The insertion electrode device according to claim 1, wherein the the safety adapter bears against a step of the probe header.

4. The insertion electrode device according to claim 3, wherein the probe header has an external screw thread, which allows the sensor probe to be screwed into an internal thread of the probe protector tube.

5. The insertion electrode device according to claim 4, wherein the coupling for the electrical leads is a plug connection, wherein a sleeve of one part of the plug connection can be screwed onto the other part of the plug connection.

6. The insertion electrode device according to claim 5, wherein the protective sleeve can be releasably fastened to the safety adapter.

7. The insertion electrode device according to claim 6, wherein said means of the safety adapter has a ring-shaped collar to reach over the step or to reach into a recess of the sensor probe.

8. The insertion electrode device according to claim 6, wherein said means of the safety adapter has at least two projections to reach over the step or to reach into a recess of the sensor probe.

9. The insertion electrode device according to claim 6, wherein said means of the safety adapter has at least two pin-shaped spring elements to reach over the step or to reach into a recess of the sensor probe.

10. The insertion electrode device according to claim 6, wherein said means of the safety adapter has a ring-shaped spring element to reach over the step or to reach into a recess of the sensor probe.

11. The insertion electrode device according to claim 1, wherein the coupling for the electrical leads is a plug connection, wherein a sleeve of one part of the plug connection is screwed onto the other part of the plug connection.

12. The insertion electrode device according to claim 1, wherein the protective sleeve is releasably fastened to the safety adapter.

13. The insertion electrode device according to claim 1, wherein said means of the safety adapter has a ring-shaped collar to reach over the step or to reach into a recess of the sensor probe.

14. The insertion electrode device according to claim 1, wherein said means of the safety adapter has at least two projections to reach over the step or to reach into a recess of the sensor probe.

15. The insertion electrode device according to claim 1, wherein said means of the safety adapter has at least two pin-shaped spring elements to reach over the step or to reach into a recess of the sensor probe.

16. The insertion electrode device according to claim 1, wherein said means of the safety adapter has a ring-shaped spring element to reach over the step or to reach into a recess of the sensor probe.

17. A method for manufacturing an insertion electrode device that includes a probe housing configured for attachment to a container, a probe protector tube that receives, holds, and guides a sensor probe, a safety adapter that is coupled to an end of the probe protector tube the safety adapter having a means for preventing bi-axial movement of the sensor probe, said means being configured to interact with the sensor probe by one of engaging a recess of the sensor probe or reach over a step of the sensor probe, wherein the probe housing has a protective sleeve configured for connection to the probe protector tube to protect the electrical coupling from mechanical stress and moisture, the method comprising:
    inserting the sensor probe into the probe protector tube up to the probe header; and
    installing the safety adapter over an end of the probe protector tube and over a portion of the probe header that protrudes from the end of the probe protector tube, wherein the safety adapter is screwed onto the probe protector tube so that the collar of the safety adapter is over the portion of the probe header.

* * * * *